| United States Patent [19] | [11] | 4,053,469 |
|---|---|---|
| Yoshioka et al. | [45] | Oct. 11, 1977 |

[54] INTERMEDIATES FOR THE PREPARATION OF 7-ACYLAMINO-3-OXYIMINO-METHYL-3-CEPHEM-3-CARBOXYLIC ACIDS

[75] Inventors: Mitsuru Yoshioka, Toyonaka; Masayuki Murakami, Itami; Yuji Sendo, Nishinomiya, all of Japan

[73] Assignee: Shionogi & Co., Ltd., Osaka, Japan

[21] Appl. No.: 673,882

[22] Filed: Apr. 5, 1976

Related U.S. Application Data

[62] Division of Ser. No. 446,112, Feb. 26, 1974, Pat. No. 3,987,039.

[30] Foreign Application Priority Data

Feb. 28, 1973   Japan ................................ 48-24512

[51] Int. Cl.$^2$ ............................................ C07D 501/18
[52] U.S. Cl. ........................................ 544/21; 424/246; 544/22; 544/16; 544/29
[58] Field of Search ................................ 260/243 C

[56] References Cited

U.S. PATENT DOCUMENTS

| 3,674,784 | 7/1972 | Webber | 260/243 C |
|---|---|---|---|
| 3,840,533 | 10/1974 | Dolfini et al. | 260/243 C |
| 3,917,587 | 11/1975 | Chauvette | 260/243 C |
| 3,917,588 | 11/1975 | Chauvette | 260/243 C |
| 3,987,039 | 10/1976 | Yoshioka et al. | 260/243 C |

*Primary Examiner*—Nicholas S. Rizzo
*Attorney, Agent, or Firm*—Wenderoth, Lind & Ponack

[57] ABSTRACT

An antibacterial 7-protected amino-3-oxyiminomethyl-3-cephem-4-carboxylic acid is prepared by the reaction of a 7-protected amino-3-formyl-3-cephem-4-carboxylic acid or its reactive derivatives with a hydroxylamine compound or its reactive derivatives, the process being more suitable for large scale production when coupled with fermentative production of a 3-hydroxymethyl-3-cephem-4-carboxylic acid followed by its direct oxidation.

2 Claims, No Drawings

INTERMEDIATES FOR THE PREPARATION OF 7-ACYLAMINO-3-OXYIMINOMETHYL-3-CEPHEM-4-CARBOXYLIC ACIDS

This is a division of application Ser. No. 446,112, filed Feb. 26, 1974, now U.S. Pat. No. 3,987,039.

This invention relates to a process for the preparation of a 7-protected amino-3-oxyiminomethyl-3-cephem-4-carboxylic acid (I) by the reaction of a 7-protected amino-3-formyl-3-cephem-4-carboxylic acid (II) or its reactive derivatives with a hydroxylamine compound (III) or its reactive derivatives; to some Compounds (I); and to their pharmaceutical preparations.

The process of this invention is represented by the following reaction scheme:

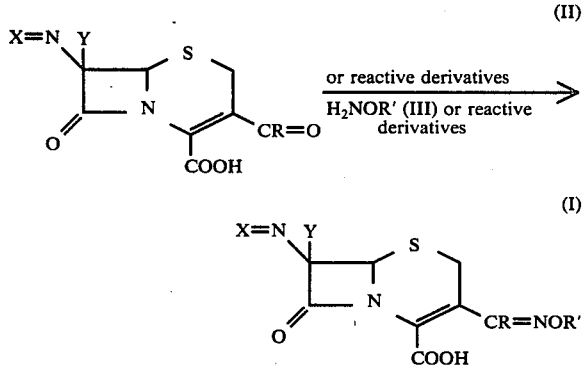

wherein X is two monovalent amino-protecting groups or a divalent amino-protecting group; Y is a hydrogen or methoxy; R is a hydrogen or methyl; R' is a hydrogen, alkyl (including cycloalkyl, aralkyl, and branched alkyl; containing 1 to 12 carbon atoms) or arly (including phenyl, naphthyl: containing 6 to 12 carbon atoms; and mono- or di-cyclic hetero-cyclic aryl containing 1 to 4 heteroatoms selected from nitrogen, oxygen, and/or sulfur), each being, where possible, optionally substituted (by halogen, alkoxy, alkylthio, alkylated amino, carboxy, carbalkoxy, optionally alkylated carbamoyl; in which alkyls contain 1 to 6 carbon atoms), and/or optionally unsaturated (e.g. alkenyl, alkynyl, cycloalkenyl, aralkenyl, aralkynyl). Typical examples of the group R' are a hydrogen, methyl, ethyl, n-propyl, isopropyl, n-butyl, isobutyl, secondary butyl, tertiary butyl, n-pentyl, secondary pentyl, neopentyl, n-hexyl, 2-chloroethyl, 2-bromoethyl, 2-chloropropyl, 3-chloropropyl, 2,3-dichloropropyl, 4-bromobutyl, 2-chlorohexyl, methoxymethyl, methoxyethyl, methoxypropyl, ethoxyethyl, norbornyloxymethyl, propoxypropyl, methylthiomethyl, methylthioethyl, methylthiopropyl, N,N-dimethylaminoethyl, cyclobutyl, cyclopentyl, cyclohexyl, cycloheptyl, 4-methylcyclohexyl, benzyl, 4-nitrobenzyl, 4-methoxybenzyl, phenyl, tolyl, xylyl, mesityl, 4-ethylphenyl, α-naphthyl, β-naphthyl, vinyl, allyl, hexenyl, cyclohexenyl, ethinyl, propargyl, carboxymethyl, methoxycarbonylmethyl, ethoxycarbonylmethyl, propoxycarbonylmethyl, hexyloxycarbonylmethyl, butoxycarbonylmethyl, carbamoylmethyl, α-carboxyethyl, α-carbethoxyethyl, α-carbamoylethyl, and α-(N-methylcarbamoyl)ethyl.

In the formulae above, one of the two monovalent amino-protecting groups represented by X is a hydrogen; alkanoyl containing 1 to 8 carbon atoms; chloro- or bromo-alkanoyl containing 2 to 8 carbon atoms; azidoacetyl; cyanoacetyl; a group of formula Ar—CQQ—CO— in which Q is a hydrogen or methyl, Ar is a thienyl, furyl, pyrrolyl, tetrazolyl, phenyl, optionally substituted by one or more chlorine, bromine, iodine, fluorine, trifluoromethyl, hydroxy, cyano, nitro, alkyl or alkoxy in which the alkyl contains 1 to 3 carbon atoms; a group of formula Ar—X"—CH₂—CO— in which Ar is as given above and X" is oxygen or sulfur; pyridylthioacetyl; a group of the formula Ar—CHX'—CO— in which Ar is as given above, and X' is (i) an amino, ammonium, carbobenzyloxyamino, alkoxycarbonylamino in which the alkyl contains 1 to 4 carbon atoms, cyclopentyloxycarbonylamino, cyclohexyloxycarbonylamino, benzhydryloxycarbonylamino, tritylamino, 2,2,2-trichloroethoxycarbonylamino, guanylcarbamoylamino, sulfoamino, phthalimido, amino group protected by enamine form of lower alkyl acetoacetate or acetylacetone, (ii) hydroxy, alkanoyloxy in which the alkanoyl contains 1 to 6 carbon atoms, (iii) carboxy, carbalkoxy in which the alkoxy contains 1 to 6 carbon atoms, or (iv) azido, cyano, or carbamoyl; sydnone-alkanoyl in which the alkanoyl part contains 2 to 3 carbon atoms; 5-aminoadipoyl, in which the amino group can be protected by an alkanoyl or haloalkanoyl containing 1–8 carbon atoms or alkoxycarbonyl, and the carboxy group can be protected by benzhydryl, 2,2,2-trichloroethyl, nitrobenzyl, or alkyl containing 4 to 6 carbon atoms; arylsulfenyl; or optionally substituted alkoxycarbonyl containing 1–12 carbon atoms (e.g. 2,2,2-trichloroethoxycarbonyl, isobornyloxycarbonyl); and the other monovalent amino-protecting group represented by X is a hydrogen or the said acyl. Typical examples of these are a formyl, acetyl, propionyl, butyryl, valeryl, hexanoyl, enanthoyl, chloroacetyl, dichloroacetyl, bromoacetyl, cyanoacetyl, 2-furylacetyl, 1-pyrrylacetyl, 2-thienylacetyl, 1-tetrazolylacetyl, phenylacetyl, 4-hydroxy-3-chlorophenylacetyl, 4-nitrophenylacetyl, 4-trifluoromethylphenylacetyl, phenoxyacetyl, phenylthioacetyl, 4-pyridylthioacetyl, α-phenylglycyl, N-tertiary butoxycarbonyl-α-phenylglycyl, N-(2,2,2-trichloroethoxy)carbonyl-α-phenylglycyl, N-acetyl-α-phenylglycyl, α-(2-thienyl)glycyl, mandeloyl, 0-(2-nitrobenzoyl)mandeloyl, α-phenyl-α-carboxyacetyl, α-(2-thienyl)-α-carboxyacetyl, α-(3-thienyl)-α-carboxyacetyl, 2-sydnone-3-acetyl, 5-aminoadipoyl, 5-tertiary butoxycarbonylaminoadipoyl, 2,2,2-trichloroethoxycarbonyl, tertiary butoxycarbonyl, isobornyloxycarbonyl, phenylthio, and 2-nitrophenylsulfenyl. The divalent amino-protecting group represented by X includes a diacyl group derived from a dibasic acid containing 3 to 12 carbon atoms; arylalkylidene containing 1 to 8 carbon atoms; a group of formula

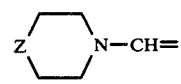

in which Z is a methylene, ethylene, or oxygen; or together with the attached nitrogen atom forms imidazolidine ring system optionally substituted by Ar given above, alkyl containing 1 to 6 carbon atoms, and/or oxo group. Typical examples of these are succinoyl, glutaroyl, phthaloyl, pyrazinedioyl, maleoyl, benzylidene, salicylidene, 1-piperidinylmethylidene, N,N-hexamethyleneaminomethylidene, 1-morpholinylmethylidene, or together with the nitrogen attached to the cephem ring, a group forming 2,2-dimethyl-4-phenyl-5- oxoimidazolidin-1-yl. Y is a hydrogen or methoxy; and R is a hydrogen or methyl.

Usually, Compound (II) tends to cyclize forming a hemiacetal lactone represented by the formula as follows:

"hemiacetal lactone"

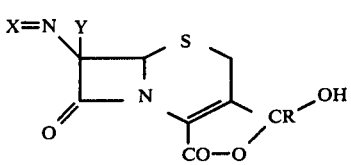

which is as reactive as the corresponding Compound (II) under the reaction conditions of this invention. Other reactive derivatives of Compound (II) include O-lower alkyl hemiacetal lactone, O-lower alkanoyl hemiacetal lactone, di-lower alkyl acetal, diacylacetal, the salts at carboxy group or group X, and other reactive derivatives equivalently utilizable in this reaction. The reactive derivatives of Compound (III) include a salt with organic or inorganic acid among which the salt with a mineral acid is used more conveniently. Other reactive derivatives of Compound (III) include a N-carbonic acyl derivative, reactive oxime, and other reactive derivatives equivalently utilizable in this reaction. When the group R' has a reactive group, it can be protected with a suitable protecting group in the art.

Compound (I) is prepared by the reaction of Compound (II) or its reactive derivatives with Compound (III) or its reactive derivatives. The reaction is carried out in a solvent, if required in the presence of an acid or base for adjusting pH or as catalyzer. The solvent for this reaction can be a hydrocarbon (e.g. pentane, hexane, heptane, cyclohexane, benzene, toluene, xylene), halohydrocarbon (e.g. methylene chloride, chloroform, carbon tetrachloride), ether (e.g. diethyl ether, dioxane, anisole, ethylene glycol dimethyl ether), ester (e.g. ethyl acetate, propyl acetate, methyl benzoate), alcohol (e.g. methanol, ethanol, propanol, isopropanol, isobutanol, butanol, benzylalcohol), carboxylic acid (e.g. formic acid, acetic acid, propionic acid), base (e.g. trialkylamine, pyridine, quinoline), amide (e.g. dimethylformamide, dimethylacetamide, hexamethylphosphoramide), nitrile (e.g. acetonitrile, propiononitrile, benzonitrile), nitroalkane (e.g. nitromethane, nitroethane, nitrobenzene), sulfoxide (e.g. dimethyl sulfoxide, diethyl sulfoxide, thiane-1, 1-dioxide), water, carbon disulfide, ammonia, sulfur dioxide, or other conventional solvent or their mixtures. A preferable solvent is one that can dissolve Compound (II) and that can give rapid reaction for the preparation, namely having sufficient polarity. Representative examples of the solvent include aqueous ether (e.g. tetrahydrofuran, tetrahydropyran, dioxane, ethylene glycol dimethyl ether, anisole), alcohol (e.g. methanol, ethanol, propanol, isopropanol, butanol, secondary butanol, benzyl alcohol), ester, nitrile, and nitromethane. More preferable solvent includes tetrahydrofuran, tetrahydropyran, dioxane, ethylene glycol dimethyl ether, anisole, methanol, ethanol, propanol, isopropanol, butanol, and secondary butanol, possibly in admixture with water. Usually, one to five mole equivalents, preferably one to two mole equivalents of Compound (III) is used for one mole equivalent of Compound (II). The reaction is preferably carried out at pH of range from about 4.5 to 7.5, and to maintain pH of the medium in this range, an acid, base or buffer solution can be added to the reaction medium. The acid for this purpose can be a mineral acid (e.g. hydrochloric acid, sulfuric acid, nitric acid, phosphoric acid), carboxylic acid (e.g. formic acid, acetic acid, propionic acid, oxalic acid, succinic acid, phthalic acid), or sulfonic acid (methanesulfonic acid, ethane-sulfonic acid, propanesulfonic acid, benzenesulfonic acid, toluenesulfonic acid, cation-exchange resin in H-form); and the base for this purpose can be ammonia, mono-, di- or trialkylamine (e.g. methylamine, ethylamine, diethylamine, trimethylamine, triethylamine, tripropylamine, dimethylbenzylamine), aromatic base (e.g. aniline, pyridine, collidine, picoline, quinoline), or basic salt (e.g. sodium carbonate, sodium acetate, sodium oxalate, potassium tartarate), or anion-exchange resins. When a salt of Compound (III) is used, sometimes base is added to neutralize the medium to weak acid, neutral or basic condition. Preferable reaction temperature is from $-50°$ C to 100° C, in which that of range from 0° C to 50° C is more preferable. The reaction can be stirred and/or kept under inert gas (e.g. nitrogen, carbon dioxide, argon). In a typical example, the reaction completes within 1 to 48 hours at room temperature. Most preferable results are obtained when Compound (II) (1 mole) is dissolved in a water miscible ether solvent (e.g. tetrahydrofuran or dioxane; 3 to 30 volume/weight) and mixed with Compound (III) (1-2 mole equivalents) and a mineral acid (1 to 2 mole equivalents) in water (2 to 20 volume/weight) and kept at 0° C to 50° C for 2 to 30 hours to give Compound (I) in 60 to 100% yield. The mineral acid salts of Compound (III) can replace the component mineral acid (0.5 to 1.5 mole) and the component Compound (III).

The product of the reaction is isolated from the reaction mixture by a conventional method in the art (e.g. concentration, evaporation of the solvent, extraction, fractional extraction, partition, precipitation, countercurrent distribution, absorption, lyophylization, chromatography, crystallization), and purified by a conventional method in the art (e.g. extraction, precipitation, partition, chromatography, crystallization, salt formation).

The product can be converted to a salt, preferably a pharmaceutically acceptable salt, by the action of a base or a weak acid salt when it is in carboxylic acid form; or to a free acid by the action of an acid when it is in salt form; by a procedure conventional in the art, respectively. The pharmaceutically acceptable salt can be an alkali metal (e.g. sodium, potassium) or alkaline earth metal (e.g. magnesium, calcium) salt, or a salt with an organic base (e.g. procain, dimethylaminoethanol).

The products (I) optionally protected at their carboxy group can also be prepared by alternative methods e.g. as follows according to conventional procedures:

i. Reducing the corresponding 1-oxide with e.g. a hydrogen in the presence of catalyzer; stannous, ferrous, cuprous, or manganous cation; iodide, ferrocyanide, or hypodithionate anion; trivalent phosphorous compound; halosilane compound; or chloromethyleneimmonium halide, preferably in a suitable solvent.

ii. Removing the carboxy-protecting group by e.g. with a hydrolysing reagent (e.g. acid including mineral acid, trifluoroacetic acid, toluene-p-sulfonic acid, etc., in water; or base) for esters, amides, anhydrides, etc.; reducing reagent (e.g. zinc or tin) for β-haloester; or hydrogenolysis with hydrogen in the presence of catalyzer for benzyl esters; or ultra-violet irradiation for phenacyl esters.

iii. Introducing 7-amino-protecting group X with e.g. corresponding acid halide, anhydride, active ester, active amide, or free acid in the presence of a condensing reagent e.g. dicyclohexyl carbodiimide, for acyl; or suitable carbonyl compounds for alkylidene.

iv. Removing 7-amino-protecting group X with e.g. hydrolyzing reagent (e.g. phosphorous pentachloride and methanol and water; nitrosyl halide and acid) for acyl; reducing reagent (e.g. zinc) for β-haloalkoxycarbonyl; or hydrogenolyzing reagent (e.g. hydrogen in the presence of catalyzer) for benzyloxycarbonyl; or acid or base (e.g. trifluoroacetic acid) for sensitive acyl groups (benzhydryloxycarbonyl, isobornyloxycarbonyl, or tertiary butoxycarbonyl).

v. Removing a protective group in the group X or R' by e.g. hydrogenolysis, hydrolysis, or reduction for amino-protecting acyl silyl, sulfenyl, alkylidene, etc. groups; hydrolysis with acid, base, etc., hydrogenolysis with hydrogen in the presence of catalyzer, reduction with reducing metal, or like methods for a hydroxy-protecting acyl, ether, or acetal etc. groups; or hydrolysis with acid or base, hydrogenolysis, photochemical irradiation, etc., for a carboxy-protecting group; as is given above items (ii)–(iv).

Even when above processes (i) to (v) are taken into consideration, the process of this invention, when coupled with fermentative deacetylation of cephalosporins followed by direct oxidation to give Compounds (II), constitutes most practical and shortest procedure suitable for large scale production of objective Compounds (I).

The antibacterial products (I) can be used as medicines for humans and warm blooded animals optionally in admixture with a conventional pharmaceutical carrier. They can be used for the prevention or treatment of bacterial infection caused by sensitive Gram positive and negative bacteria, especially weakly cephalosporin-resistant E. coli and Proteus mirabilis, at a dose of 0.01 to 1g per kilogram body weight per day, preferably in a unit dosage form. They can be used for the treatment of plant diseases caused by bacteria, or for the prevention of or stopping of decay of perishables. They are also useful as intermediates for the production of other antibacterials. The pharmaceutical carrier for the compounds can be a solid or liquid in which the compounds are dissolved, dispersed, or suspended. Solid compositions can take the form of tablets, powders, vials, granules, capsules, pills or the like forms. Liquid compositions can take the form of injections, ointments, suspensions, solutions, emulsions, syrups, elixirs, or like forms. Preparations can be flavoured, coloured, or coated. The carriers can include diluents (e.g. starch, sucrose, lactose, calcium carbonate, kaolin); colouring agents; aromatic substances; bulking agents (e.g. lactose, salt, glycine, starch, calcium carbonate, kaolin, bentonite, calcium phosphate); binders (e.g. starch, acacia, gelatin, glucose, socium aliginate, tragacanth, carboxymethylcellulose); disintegrators (e.g. starch, agar, carbonates); lubricants (e.g. stearic acid, talc, paraffin, boric acid, sodium benzoate, Carbowax, cacao oil); ointment bases (e.g. fats, oils, lard, wool fat, vaselin, glycerin, resins, glycols); emulsifying agents; solvents (e.g. water, polyethylene glycol, olive oil, sesame oil, cacao oil, methyl or ethyl oleate); solubilizing agents; buffers, and stabilizing agents. Vials for injection and capsules for oral administration can contain pure powder, lyophylizate, or crystals or Compound (I) (0.05 – 10 g), together with additives such as stabilizers or co-acting substances, if required. Ointments and powders can contain 0.001 – 10% of Compound (I).

Among Compounds (I), those with the following formulae and their pharmaceutically acceptable salts are novel antibacterial compounds of cephalosporin type:

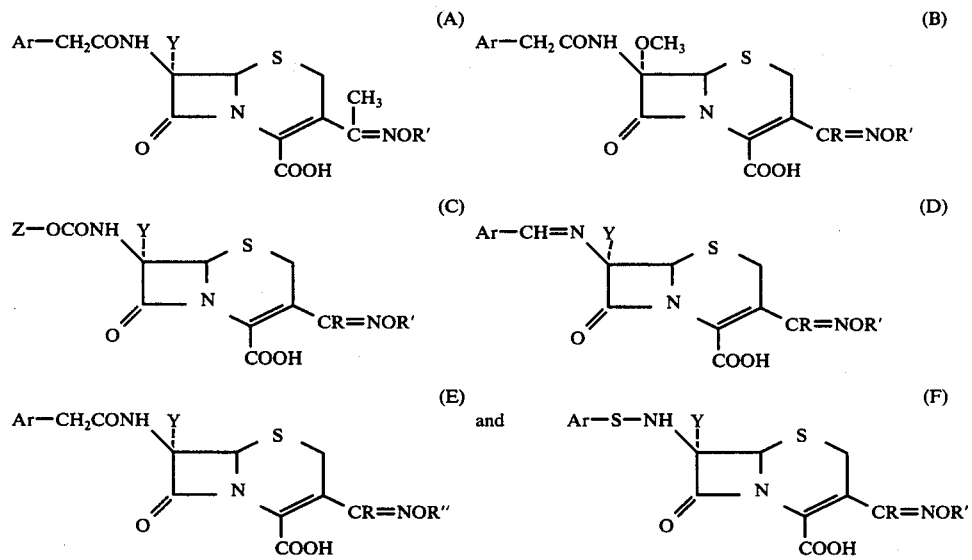

wherein Ar, Y, R, and R' are as defined above; R" is an alkenyl, alkynyl, aralkyl, or optionally substituted carbamoylmethyl, each as defined in the definition of R'; and Z is an optionally substituted alkyl containing 1–12 carbon atoms.

Representatives of the said compounds are the following compounds:

A. 3-(α-oxyiminoethyl)-cephem-4-carboxylic acids

Preferable Compound (A) has a hydrogen for Y; and/or thienyl or phenyl for Ar.

3-(α-methoxyiminoethyl)-7β-(2-thienylacetamido)-3-cephem-4-carboxylic acid,
3-(α-methoxyiminoethyl)-7β-(2-thienylacetamido)-3-cephem-4-carboxylic acid,
3-(α-carboxymethoxyiminoethyl)-7β-(2-thienylacetamido)-3-cephem-4-carboxylic acid.
3-(α-carboxymethoxyiminoethyl)-7β-phenylacetamido-3-cephem-4-carboxylic acid, B.
7-methoxy-3-oxyiminomethyl-3-cephem-4-carboxylic acids Preferable Compound (B) has a hydrogen for R; and/or thienyl or phenyl for Ar.

3-methoxyiminomethyl-7α-methoxy-7β-(2-thienylacetamido)-3-cephem-4-carboxylic acid,
3-carboxymethoxyiminomethyl-7α-methoxy-7β-(2-thienylacetamido)-3-cephem-4-carboxylic acid,
3-methoxycarbonylmethoxyiminomethyl-7α-methoxy-7β-(2-thienylacetamido)-3-cephem-4-carboxylic acid,
3-carbamoylmethoxyiminomethyl-7α-methoxy-7β-(2-thienylacetamido)-3-cephem-4-carboxylic acid,
3-methoxyiminomethyl-7α-methoxy-7β-phenylacetamido-3-cephem-4-carboxylic acid, C. 7-carbonic acylamino-3-oxyiminomethyl-3-cephem-4-carboxylic acids Preferable Compound (C) has a 2,2,2-trichloroethyl, isobornyl, or cyclohexyl for Z; and/or hydrogen for Y.

7β-(2,2,2-trichloroethoxycarbonyl)amino-3-methoxyiminomethyl-3-cephem-4-carboxylic acid,
7β-isobornyloxycarbonylamino-3-methoxyiminomethyl-3-cephem-4-carboxylic acid,
7β-methoxycarbonylamino-3-ethoxyiminomethyl-3-cephem-4-carboxylic acid,
7β-cyclohexyloxycarbonylamino-3-allyloxyiminomethyl-3-cephem-4-carboxylic acid,
7β-cyclopentyloxycarbonylamino-3-carboxymethoxyiminomethyl-3-cephem-4-carboxylic acid, D.
7-arylmethylideneamino-3-oxyiminomethyl-3-cephem-4-carboxylic acids.

Preferable Compound (D) has a 2-hydroxyphenyl for Ar.

7β-benzylideneamino-3-methoxyiminomethyl-3-cephem-4-carboxylic acid,

7β-salicylideneamino-3-methoxyiminomethyl-3-cepham-4-carboxylic acid,

E.
3-alkenyl-, alkynyl-, aralkyl- or optionally substituted carbamoylmethoxyiminomethyl-7-arylacetamido-3-cephem-4-carboxylic acids Preferable Compound (E) has a hydrogen for Y; a hydrogen for R; and/or thienyl, tetrazolyl, or phenyl for Ar.

3-allyloxyiminomethyl-7β-(2-thienylacetamido)-3-cephem-4-carboxylic acid,
3-ethinyloxyiminomethyl-7β-(2-thienylacetamido)-3-cephem-4-carboxylic acid,
3-propargyloxyiminomethyl-7β-phenylacetamido-3-cephem-4-carboxylic acid,
3-benzyloxyiminomethyl-7β-(2-thienylacetamido)-3-cephem-4-carboxylic acid,
3-p-methoxybenzyloxyiminomethyl-7β-(1-tetrazolyl)acetamido-3-cephem-4-carboxylic acid,
3-carbamoylmethoxyiminomethyl-7β-(2-thienylacetamido)-3-cephem-4-carboxylic acid,
3-(N-methylcarbamoyl)methoxyiminomethyl-7β-furylacetamido-3-cephem-4-carboxylic acid, and F.
7-sulfenylamino-3-oxyiminomethyl-3-cephem-4-carboxylic acids Preferable Compound (F) has o-nitrophenyl for Ar.

7β-(o-nitrophenylsulfenylamino)-3-methoxyiminomethyl-3-cephem-4-carboxylic acid.

Compounds (A), (B), and (E) are strong antibacterials for the treatment or prevention of infections by Gram positive and negative bacteria sensitive to the compounds, in a manner cited before relating to use of the products of this invention.

Compounds (C), (D), and (F) are also antibacterials for mainly Gram positive bacteria, but they are more useful as intermediates for the preparation of other antibacterials, e.g. Compounds (I), especially compounds (B) or (E).

The pharmaceutically acceptable salts are alkali metal (e.g. sodium, potassium), alkaline earth metal (e.g. magnesium, calcium) or organic base (e.g. procain, dimethylaminoethanol) salts.

Other new compounds are those represented by the following formulae:

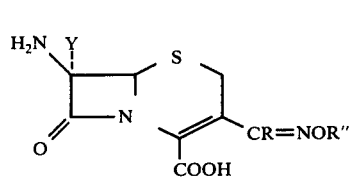
(A')

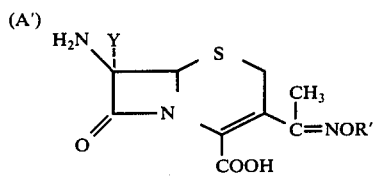
(B')

and

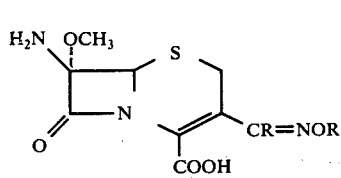
(C')

wherein Y, R, R', and R" are as defived above, and their derivatives protected at the carboxyl group and/or amino group. These compounds are used for the preparation of 7-acylamino-3-oxyiminomethyl-3-cephem-4-carboxylic acids useful as antibacterials as stated above, by the introduction of an acyl group at the amino group located at position 7.

Preferable Compound (A') has a hydrogen for Y; and/or a hydrogen for R; preferable Compound (B') has a hydrogen for Y; and preferable Compound (C') has a hydrogen for R.

Typical examples of these are the following compounds:

A'.
7β-Amino-3-oxyiminomethyl-3-cephem-4-carboxylic acids 3-allyloxyiminomethyl-7β-amino-3-cephem-4-carboxylic acid,
3-ethinyloxyiminomethyl-7β-amino-3-cephem-4-carboxylic acid,
3-propargyloxyiminomethyl-7β-amino-3-cephem-4-carboxylic acid,
3-benzyloxyiminomethyl-7β-amino-3-cephem-4-carboxylic acid,
3-(p-methoxybenzyl)oxyiminomethyl-7β-amino-3-cephem-4-carboxylic acid,
3-carbamoylmethoxyiminomethyl-7β-amino-3-cephem-4-carboxylic acid,
3-(N-methylcarbamoyl)methoxyiminomethyl-7β-amino-3-cephem-4-carboxylic acid, B'.
7β-Amino-3-(α-oxyimino)ethyl-3-cephem-4-carboxylic acids 3-(α-methoxyiminoethyl)-7β-amino-3-cephem-4-carboxylic acid,
3-(α-ethoxyiminoethyl)-7β-amino-3-cephem-4-carboxylic acid,
3-(α-carboxymethoxyiminoethyl)-7β-amino-3-cephem-4-carboxylic acid,
3-(α-carbamoylmethoxyiminoethyl)-7β-amino-3-cephem-4-carboxylic acid, C'.
7β-Amino-7α-methoxy-3-oxyiminomethyl-3-cephem-4-carboxylic acids 3-methoxyiminomethyl-7α-methoxy-7β-amino-3-cephem-4-carboxylic acid,
3-carboxymethoxyiminomethyl-7α-methoxy-7β-amino-3-cephem-4-carboxylic acid,
3-ethoxyiminomethyl-7α-methoxy-7β-amino-3-cephem-4-carboxylic acid, and
3-(α-methoxyiminoethyl)-7α-methoxy-7β-amino-3-cephem-4-carboxylic acid.

The protecting group for the carboxylic acid group at position 4 is one conventional in the art including haloalkyl ester (e.g. 2,2,2-trichloroethyl-, 2-iodoethyl-, and 2-bromoethyl-esters), tertiary alkyl ester containing 4-6 carbon atoms (e.g. tertiary butyl ester), tertiary alkenyl or tertiary alkynyl ester with 5-7 carbon atoms, benzyl-, methoxybenzyl, or nitrobenzyl ester, 3,5-di-(tertiary butyl)-4-hydroxybenzyl ester, acetoxymethyl ester, pivaloyloxymethyl ester, benzhydryl ester, phenacyl ester, trimethylsilyl ester, succinimidomethyl ester, phthalimidomethyl ester or like esters, or reactive amides e.g. 1,2-diisopropylhydrazide, or like amides, which are cleaved conveniently by conventional methods in the art (e.g. by the action of acid, base, or hydrogen). These protecting groups can be introduced prior to, or after the reaction of this invention, and can be cleaved prior to or after the introduction of an acyl group at the 7-amino group.

The following examples represent presently-preferred embodiments of this invention, but it is to be understood that the examples are given by way of illustration only and not of limitation. The elemental analyses of the compounds as prepared show good agreement with the calculated values. EtOH is for ethanol, and DMSO is for dimethyl sulfoxide.

EXAMPLE I

To a solution of 3-formyl-7β-(2-thienylacetamido)-3-cephem-4-carboxylic acid (35 mg) in tetrahydrofuran (3 ml) is added a solution of O-methylhydroxylamine hydrochloride (13 mg) in water (1.5 ml), and the mixture is left standing for 24 hours. After evaporation of the tetrahydrofuran at room temperature, the separated yellow oil is extracted with ethyl acetate. The extract solution is washed with water, dried and evaporated to leave pale yellow foam which gives crystals of 3-methoxyiminomethyl-7β-(2-thienylacetamido)-3-cephem-4-carboxylic acid (37 mg; nearly quantitative yield) by recrystallization from ether and ethyl acetate. m.p. 186°-189° C.

EXAMPLE II

Using a procedure similar to that in Example I, the following reactions are carried out with the variations specified. The results are illustrated in Table I. The available physical constants of the products are listed in Table II. All starting compounds and compounds produced have a 7β-nitrogen side chain.

TABLE I
REACTION OF EXAMPLE II

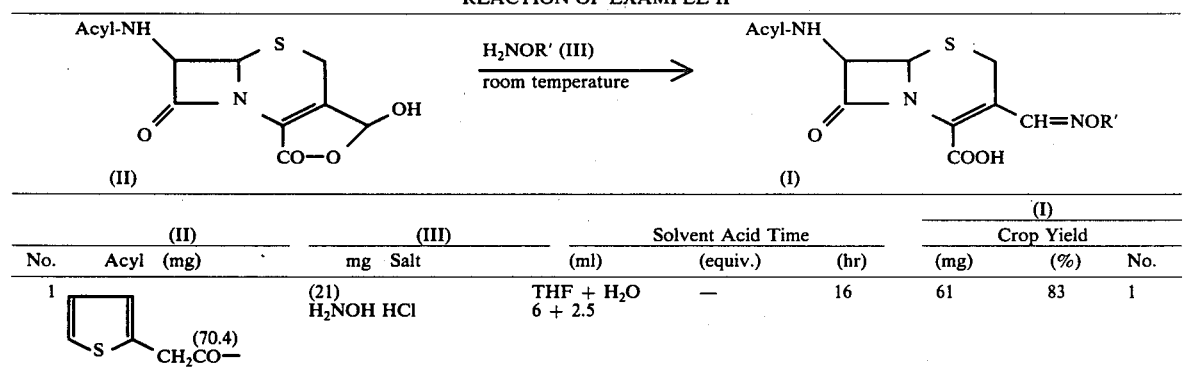

| | (II) | | (III) | | Solvent | Acid | Time | (I) | | |
|---|---|---|---|---|---|---|---|---|---|---|
| | | | | | | | | Crop | Yield | |
| No. | Acyl | (mg) | mg | Salt | (ml) | (equiv.) | (hr) | (mg) | (%) | No. |
| 1 | S-CH₂CO— | (70.4) | (21) H₂NOH HCl | | THF + H₂O 6 + 2.5 | — | 16 | 61 | 83 | 1 |

TABLE I-continued

REACTION OF EXAMPLE II

Acyl-NH—[β-lactam]—CO—O (II) + H₂NOR' (III) —room temperature→ Acyl-NH—[β-lactam]—CH=NOR', COOH (I)

| | (II) | | (III) | | Solvent | Acid | Time | (I) Crop Yield | | |
|---|---|---|---|---|---|---|---|---|---|---|
| No. | Acyl | (mg) | mg Salt | | (ml) | (equiv.) | (hr) | (mg) | (%) | No. |
| 2 | thiophene-CH₂CO— | (704) | (249) H₂NOCH₃ HCl | | THF + H₂O 70 + 25 | — | 19 | 505 | 60.3 | 2a |
| 3 | thiophene-CH₂CO— | (141) | (59) H₂NOC₂H₅ HCl | | THF + H₂O 12 + 5 | — | 18 | 112 | 71 | 3 |
| 4 | thiophene-CH₂CO— | (141) | (67) HCl H₂NOCH(CH₃)₂ | | THF + H₂O 12 + 5 | — | 24 | 108 | 66 | 4 |
| 5 | thiophene-CH₂CO— | (141) | (75.4) HCl H₂NOCH₂CH(CH₃)₂ | | THF + H₂O 12 + 5 | — | 24 | 106 | 63 | 5 |
| 6 | thiophene-CH₂CO— | (141) | (91) HCl H₂NOCH(CH₂)₅ | | THF + H₂O 12 + 5 | — | 21 | 102 | 56.6 | 6 |
| 7 | thiophene-CH₂CO— | (141) | (66) HCl H₂NOCH₂CH=CH₂ | | THF + H₂O 12 + 5 | — | 21 | 100 | 61.5 | 7 |
| 8 | thiophene-CH₂CO— | (141) | (66) H₂NOCH₂C≡CH HCl | | THF + H₂O 12 + 5 | — | 18 | 120 | 74 | 8 |
| 9 | thiophene-CH₂CO— | (141) | (97.5) H₂NOCH₂C₆H₅ HCl | | THF + H₂O 12 + 5 | — | 16 | 138 | 75 | 9 |
| 10 | thiophene-CH₂CO— | (94) | (58) H₂NOC₆H₅ HCl | | THF + H₂O 8 + 3 | — | 23 | 63.7 | 48 | 10 |
| 11 | thiophene-CH₂CO— | (4950) | (3700) ½ HBr H₂NOCH₂COOH | | THF + H₂O 240 + 45 | HCl (14ml) | 1.5 | 4470 | 75 | 11 |
| 12 | thiophene-CH₂CO— | (439) | (157) H₂NOCH₂COOCH₃ | | THF + H₂O 40 + 11 | HCl 1.2 | 3 | 447 | 81.8 | 12 |
| 13 | thiophene-CH₂CO— | (211) | (107) H₂NOCH₂COOC₂H₅ | | THF + H₂O 21 + 5 | HCl 1.5 | 2 | 145 | 53 | 13 |
| 14 | thiophene-CH₂CO— | (211) | (152) HCl H₂NOCH₂CONH₂ | | THF + H₂O 21 + 6 | — | 3 | 150 | 59 | 14 |
| 15 | thiophene-CH₂CO— | (352) | (279) HBr H₂NOCH(CH₃)COOH | | THF + H₂O 35 + 6 | — | 2 | 117 | 27 | 15 |

TABLE I-continued
REACTION OF EXAMPLE II $$\text{Acyl-NH} \begin{array}{c} \text{S} \\ \text{N} \\ \text{O} \end{array} \begin{array}{c} \text{CH}_2 \\ \text{OH} \\ \text{CO-O} \end{array} \xrightarrow[\text{room temperature}]{\text{H}_2\text{NOR' (III)}} \text{Acyl-NH} \begin{array}{c} \text{S} \\ \text{N} \\ \text{O} \end{array} \begin{array}{c} \text{CH=NOR'} \\ \text{COOH} \end{array}$$

(II) → (I)

| | (II) | | (III) | | Solvent | Acid | Time | (I) Crop Yield | | |
|---|---|---|---|---|---|---|---|---|---|---|
| No. | Acyl | (mg) | mg | Salt | (ml) | (equiv.) | (hr) | (mg) | (%) | No. |
| 16 | [thiophene]-CH$_2$CO— | (142) | (80) H$_2$NOCHCOOC$_2$H$_5$ \| CH$_3$ | | THF + H$_2$O 14 + 1.6 | HCl 1.5 | 5 | 92.3 | 49 | 16 |
| 17 | [thiophene]-CH$_2$CO— | (70.5) | (33.4) H$_2$NOCH$_3$ HCl | | THF + H$_2$O 2.8 + 0.7 | — | 23 | 44.7 | 60.7 | 17 |
| 18 | [thiophene]-CH$_2$CO— | (70.5) | (33.4) H$_2$NOCH$_3$ HCl | | THF + H$_2$O 2.8 + 0.7 | — | 7.5 | 50 | 65.3 | 18 |
| 19 | C$_6$H$_5$CH$_2$CO— | (50.6) | (22.4) H$_2$NOH HCl | | THF + H$_2$O 5 + 1 | — | 5 | 28.3 | 54.1 | 19 |
| 20 | C$_6$H$_5$CH$_2$CO— | (141) | (66) H$_2$NOCH$_3$ HCl | | THF + H$_2$O 14 + 2 | — | 6 | 101 | 65 | 20 |
| 21 | C$_6$H$_5$OCH$_2$CO— | (43.5) | (16.7) H$_2$NOH HCl | | THF + H$_2$O 4.4 + 1.0 | — | 4.5 | 36 | 79.5 | 21 |
| 22 | C$_6$H$_5$OCH$_2$CO— | (43.5) | (25) H$_2$NOCH$_3$ HCl | | THF + H$_2$O 5 + 1 | — | 3 | 39 | 82 | 22 |
| 23 | C$_6$H$_5$CHCO— \| NH$_2$ | (65.8) | (25) H$_2$NOCH$_3$ HCl | | THF + H$_2$O 5 + 1 | — | 2 | 56 | 78 | 23 |
| 24 | C$_6$H$_5$CHCO— \| NHCOO tert-C$_4$H'$_9$ | (184.6) | (91) HCl H$_2$NOCH (CH$_2$)$_5$ | | THF + H$_2$O 12 + 5 | — | 2 | 186 | 83 | 24 |
| 25 | C$_6$H$_5$CHCO— \| NH$_2$ | (65.8) | (30.2) HCl H$_2$NOCH (CH$_2$)$_5$ | | Dioxane + H$_2$O 10 + 3 | — | 3 | 73 | 86 | 25 |
| 26 | C$_6$H$_5$CHCO— \| NHCOO tert-C$_4$H'$_9$ | (184.6) | (106) ½ HBr H$_2$NOCH$_2$COOH | | THF + H$_2$O 10 + 2.4 | HCl 0.4 | 1.8 | 149 | 69.7 | 26 |
| 27 | C$_6$H$_5$CHCO— \| NH$_2$ | (65.8) | (106) H$_2$NOCH$_2$COOH | | THF + H$_2$O 8 + 1 | — | 3 | 58 | 72 | 27 |
| 28 | C$_6$H$_5$CHCO— \| OH | (66) | (17) H$_2$NOCH$_3$ HCl | | THF + H$_2$O 4 + 1 | — | 5 | 46 | 64 | 28 |
| 29 | N≡CCH$_2$CO— | (165) | (50) H$_2$NOCH$_3$ HCl | | THF + H$_2$O 10 + 2 | — | 3 | 133 | 75.2 | 29 |
| 30 | Cl$_3$CCH$_2$OCO— | (2825) | (877) H$_2$NOCH$_3$ HCl | | THF + H$_2$O 110 + 70 | — | 16 | 1704 | 56.3 | 30 |
| 31 | C$_6$H$_4$S— \| o-NO$_2$ | (80) | (26.2) H$_2$NOCH$_3$ HCl | | THF + H$_2$O 4.8 + 1.6 | — | 3.5 | 28.6 | 33.2 | 31 |

31 (3-(α-oxyiminoethyl)-derivative)

TABLE I-continued

REACTION OF EXAMPLE II

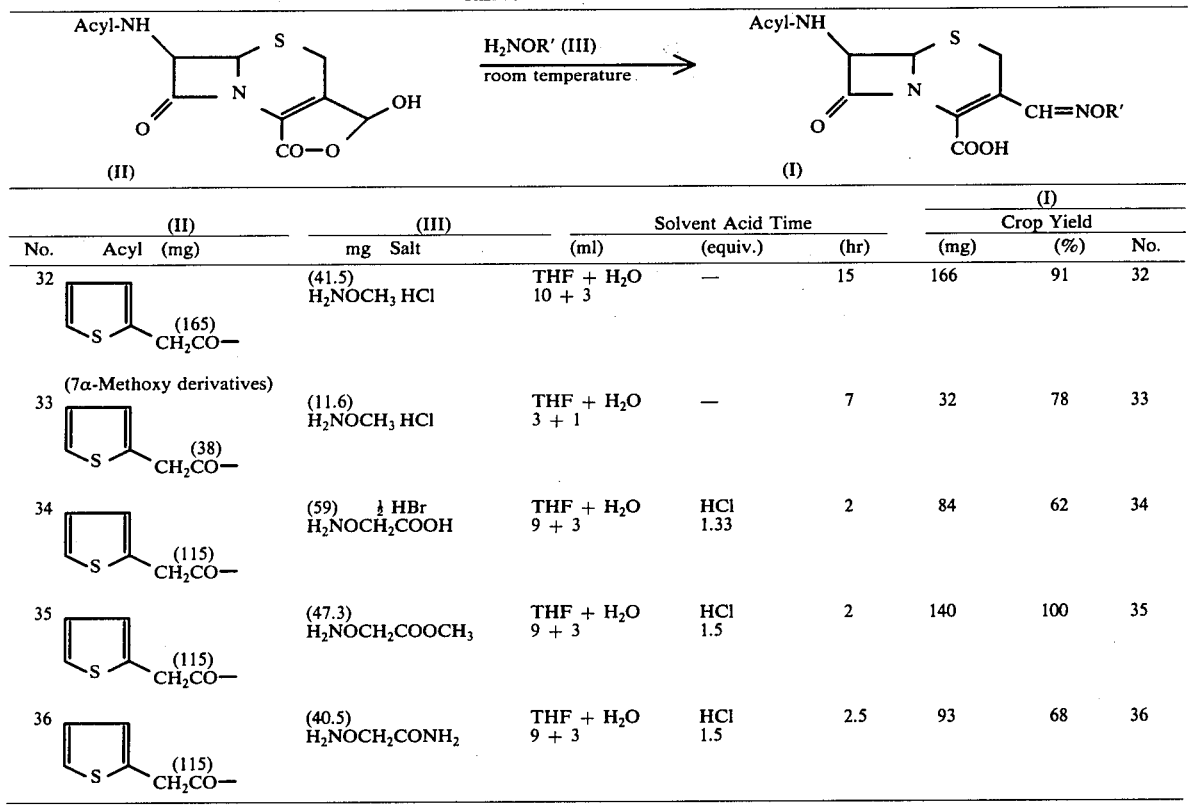

| | (II) | | (III) | Solvent | Acid | Time | (I) Crop Yield | | |
|---|---|---|---|---|---|---|---|---|---|
| No. | Acyl | (mg) | mg Salt | (ml) | (equiv.) | (hr) | (mg) | (%) | No. |
| 32 | ⌬S⌭CH₂CO— | (165) | (41.5) H₂NOCH₃ HCl | THF + H₂O 10 + 3 | — | 15 | 166 | 91 | 32 |
| | (7α-Methoxy derivatives) | | | | | | | | |
| 33 | ⌬S⌭CH₂CO— | (38) | (11.6) H₂NOCH₃ HCl | THF + H₂O 3 + 1 | — | 7 | 32 | 78 | 33 |
| 34 | ⌬S⌭CH₂CO— | (115) | (59) ½ HBr H₂NOCH₂COOH | THF + H₂O 9 + 3 | HCl 1.33 | 2 | 84 | 62 | 34 |
| 35 | ⌬S⌭CH₂CO— | (115) | (47.3) H₂NOCH₂COOCH₃ | THF + H₂O 9 + 3 | HCl 1.5 | 2 | 140 | 100 | 35 |
| 36 | ⌬S⌭CH₂CO— | (115) | (40.5) H₂NOCH₂CONH₂ | THF + H₂O 9 + 3 | HCl 1.5 | 2.5 | 93 | 68 | 36 |

TABLE II

PHYSICAL CONSTANTS OF COMPOUNDS (I)

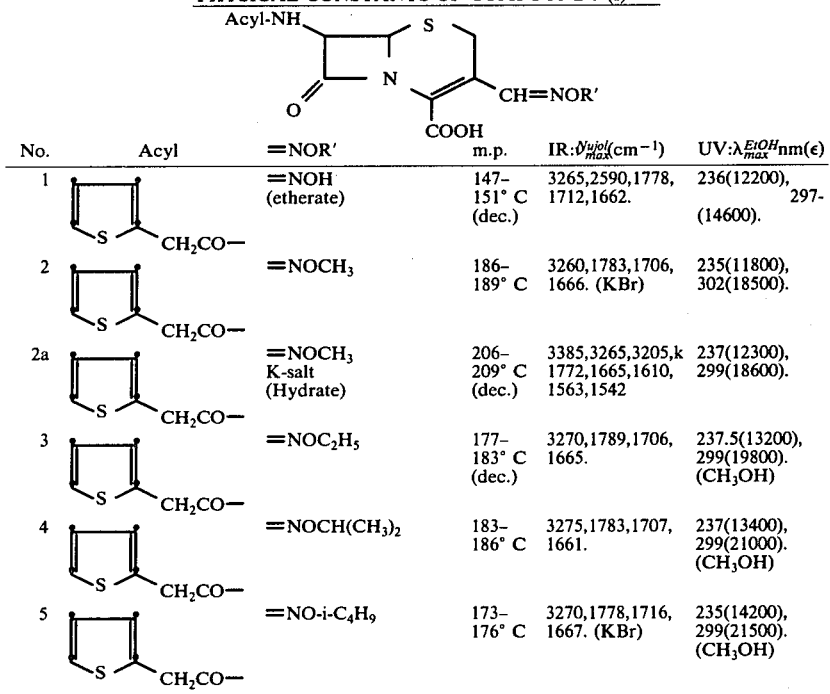

| No. | Acyl | =NOR' | m.p. | IR:$\nu_{max}^{Nujol}$(cm⁻¹) | UV:$\lambda_{max}^{EtOH}$nm(ε) |
|---|---|---|---|---|---|
| 1 | ⌬S⌭CH₂CO— | =NOH (etherate) | 147–151° C (dec.) | 3265,2590,1778, 1712,1662. | 236(12200), 297-(14600). |
| 2 | ⌬S⌭CH₂CO— | =NOCH₃ | 186–189° C | 3260,1783,1706, 1666. (KBr) | 235(11800), 302(18500). |
| 2a | ⌬S⌭CH₂CO— | =NOCH₃ K-salt (Hydrate) | 206–209° C (dec.) | 3385,3265,3205,k 1772,1665,1610, 1563,1542 | 237(12300), 299(18600). |
| 3 | ⌬S⌭CH₂CO— | =NOC₂H₅ | 177–183° C (dec.) | 3270,1789,1706, 1665. | 237.5(13200), 299(19800). (CH₃OH) |
| 4 | ⌬S⌭CH₂CO— | =NOCH(CH₃)₂ | 183–186° C | 3275,1783,1707, 1661. | 237(13400), 299(21000). (CH₃OH) |
| 5 | ⌬S⌭CH₂CO— | =NO-i-C₄H₉ | 173–176° C | 3270,1778,1716, 1667. (KBr) | 235(14200), 299(21500). (CH₃OH) |

| No. | NMR:$\delta^{d_6\text{-}DMSO}$ (Hz-Values show coupling consts.) | $[\alpha]_D^t{}^C$(c) |
|---|---|---|
| 1 | 3.77s2H,5.17d(4.8Hz)1H,5.73dd (4.8;7.8Hz)1H,8.20s1H,9.00d (7.8Hz)1H. | + 4.6° 0.262EtOH 23° C |
| 2 | 3.79ABq(27;18Hz)2H,3.08s2H, 3.88s3H,5.20d(4.8Hz)1H,5.78d | − 171.8° 0.344CHCl |

TABLE II-continued
PHYSICAL CONSTANTS OF COMPOUNDS (I)

Structure: Acyl-NH on β-lactam fused to dihydrothiazine with =CH—NOR′ and COOH substituents.

| No. | NMR / other data | [α] / solvent / temp |
|---|---|---|
| | (4.8Hz)1H,8.26s1H. (+D$_2$O) | 21° C |
| 2a | ca.3.67-2H,3.88s5H,5.17d(5Hz)1H,5.67d(5Hz)1H,6.92-7.5m3H,8.13s1H. (D$_2$O) | −23.1°, 1.004H$_2$O, 24° C |
| 3 | 1.28t(7Hz)3H,3.79ABq2H,3.85s2H,4.28q(7Hz)2H,5.04d(5Hz)1H,5.82d(5Hz)1H,8.46s1H.(CDCl$_3$+CD$_3$OD) | −50.3°, 0.376CH$_3$OH, 21.5° C |
| 4 | 1.25d(6.5Hz)6H,2.12ABq2H,2.15s2H,5.02d(5Hz)1H,5.77d(5Hz)1H 6.9-7.3m3H,8.40s1H.(CDCl$_3$+CD$_3$OD) | −43.6°, 0.273CH$_3$OH, 22.5° C |
| 5 | 0.92d(6.5Hz)6H,1.98sept(6.5Hz)1H,3.74ABq2H,3.82s2H,3.87d(6.5Hz)2H,5.old(5Hz)1H,5.78d(5Hz)1H,6.9-7.3m3H,8.43s1H. (CDCl$_3$+CD$_3$OD) | −44.9°, 0.323CH$_3$OH, 22.5° C |

| No. | Acyl | =NOR′ | m.p. | IR:ν$_{max}^{Nujol}$(cm$^{-1}$) | UV:λ$_{max}^{EtOH}$nm(ε) |
|---|---|---|---|---|---|
| 6 | thiophene-CH$_2$CO— | =NOCH(CH$_2$)$_5$ | 165–175° C | 3285,1781,1731 1711,1666. | 237(12400), 300(21000), (CH$_3$OH) |
| 7 | thiophene-CH$_2$CO— | =NOCH$_2$CH=CH$_2$ | 173–180° C | 3270,1792,1705, 1666. | 237(13400), 299(21500). (CH$_3$OH) |
| 8 | thiophene-CH$_2$CO— | =NOCH$_2$C≡CH | 183–185° C (dec.) | 3280,3260,2120, 1795,1702,1677. | 238(12300), 298(20100). (CH$_3$OH) |
| 9 | thiophene-CH$_2$CO— | =NOCH$_2$C$_6$H$_5$ (1/3etherate) | 155–161° C | 3275,4783,1712, 1663,1602. | 236(17400), 300(21000). |
| 10 | thiophene-CH$_2$CO— | =NOC$_6$H$_5$ | 167–170° C (dec.) | 3260,1784,1725, 1665,1590. | 227(16000), 2795(10400), 3115(23100). |
| 11 | thiophene-CH$_2$CO— | =NOCH$_2$COOH | 158–168° C (dec.) | 3270,1780,1725, 1688,1655,1600. 1535. | 237(12200), 300(19000). (CH$_3$OH) |
| 12 | thiophene-CH$_2$CO— | =NOCH$_2$COOCH$_3$ | 82–92° C | 3500,3280,1780, 1760,1720,1660, 1530 | 236(11500), 300(16100). |
| 13 | thiophene-CH$_2$CO— | =NOCH$_2$coO—C$_2$H$_5$ | 165–168° C (dec.) | 3575,3250,1808, 1760,1725,1668, 1605,1533 | 301(15700), 235(12900). |
| 14 | thiophene-CH$_2$CO— | =NOCH$_2$CONH$_2$ | 115–120° C | 3300,1785,1665, 1605,1532. | 301(14200), 235(10900). |

| No. | NMR:δ$^{d_6DMSO}$ (Hz-value show coupling consts.) | [α]$_D^{t°}$(c) |
|---|---|---|
| 6 | 1.0–2.2mlOH,3.82ABq2H,3.83s2H. 4.25br1H,5.06d(4.8Hz)1H,5.77d (4.8Hz)1H,8.47s1H.(CDCl$_3$+CD$_3$OD) | −43.2°, 0.359CH$_3$OH, 20.5° C |
| 7 | 3.82ABq2H,3.83s2H,4.5–4.8(2H), 5.15d(4.8Hz)1H,5.42d(5.5Hz)2H, 5.83d(4.8Hz)1H,5.7–6.4mlH,8.48 s1H. (CDCl$_3$+CD$_3$OD) | −44.2°, 0.172CH$_3$OH, 20.5° C |
| 8 | 2.59t(2.3Hz)1H,3.78ABq2H,3.82s 2H,4.22d(2.3Hz)2H,5.07d(5Hz)1H, 5.81d(5Hz)1H,6.9–7.4m3H,8.50s 1H. (CDCl$_3$+CD$_3$OD) | −56.5°, 0.407CH$_3$OH, 24.0° C |
| 9 | 3.77ABq2H,3.85s2H,5.03d(5Hz)1H, 5.85d(5Hz)1H,6.9–7.4m3H,8.68s 1H. (CDCl$_3$+CD$_3$OD) | −132.8°, 1.001CHCl$_3$, 23.0° C |
| 10 | 3.85s2H,3.88ABq2H,5.07d(5Hz)1H, 5.83d(5Hz)1H,6.9–7.4m3H,8.78s 1H. (CDCl$_3$+CD$_3$OD) | −89.6°, 0.268CH$_3$OH, 20.0° C |
| 11 | 3.73ABq(24;18Hz)2H,4.62s2H,5.0 d(5Hz)1H,5.77dd(8;5Hz)1H,6.9– 7.5m3H,8.30s1H,9.13d(8Hz)1H. | −47.0°, 0.277CH$_3$OH, 24.0° C |
| 12 | 3.73s3H,3.83s2H,4.73s2H,5.12d | −45.8° |

TABLE II-continued

PHYSICAL CONSTANTS OF COMPOUNDS (I)

Acyl-NH—[β-lactam-thiazine]—CH=NOR', COOH

| | | | | | |
|---|---|---|---|---|---|
| | | (4Hz)1H,5.80dd(4;8Hz)1H,6.8-7.5m3H,8.33s1H,9.20d(8Hz)1H. | | | 0.293DMSO 23° C |
| | 13 | ——— | | | −63.5° 0.307DMSO 23.0° C |
| | 14 | 3.80s2H,4.47s2H,5.20d(5Hz)1H, 5.80dd(5;8Hz)1H,6.8-7.5m3H,8.33 s1H,8.92d(8Hz)1H. | | | −31.2° 0.314DMSO 23° C |

| No. | Acyl | =NOR' | m.p. | IR:$\nu_{max}^{Nujol}$(cm$^{-1}$) | UV:$\lambda_{max}^{EtOH}$nm($\epsilon$) |
|---|---|---|---|---|---|
| 15 | [thiophene]-CH$_2$CO— | —NOCHCOOH \| CH$_3$ | 120–130° C | 3500,3300,1787, 1730,1670,1610, 1530 | 303(15200), 234(12900). |
| 16 | [thiophene]-CH$_2$CO— | =NOCHCOOC$_2$H$_5$ \| CH$_3$ | 100–110° C | 3280,1785,1730, 1670,1605,1530. | 235(23200), 302(29500). |
| 17 | [furan]-CH$_2$CO— | =NOCH$_3$ | 188–193° C (dec.) | 3585,3265,1776, 1742,1722,1688, 1659,1599,1536. | 301(18100). |
| 18 | [thiophene]-CH$_2$CO— | =NOCH$_3$ | 170–180° C (dec.) | 3525,3254,1781, 1723,1654,1600, 1536. | 301(17500). |
| 19 | C$_6$H$_5$CH$_2$CO— | =NOH (Hydrate) | 130°–145° C (dec.) | 3245,1775,1703, 1660,1600,1535, 1498. | 295(9900). |
| 20 | C$_6$H$_5$CH$_2$CO— | =NOCH$_3$ | 158–165° C | 3400,3300,1788, 1682,1603,1503. | — |
| 21 | C$_6$H$_5$OCH$_2$CO— | =NOH (Hydrate) | 117–133° C (dec.) | 3304,1786,1715, 1678,1599,1532. | 297(12100). |
| 22 | C$_6$H$_5$OCH$_2$CO— | =NOCH$_3$ | 93–98° C | 3400,1792,1701, 1603,1563,1512 1493.(CHCl$_3$) | — |

| No. | NMR:$\delta^{d_6-DMSO}$ (Hz-Values show coupling consts.) | $[\alpha]_D^{t,C}$(c) |
|---|---|---|
| 15 | 1.37d(7Hz)3H,3.77s2H,5.20d(5Hz) 1H,5.92m2H,6.7-7.7m3H,8.27s1H, 8.83d(8Hz)1H. | −77.2° 0.315DMSO 23° C |
| 16 | 1.20t(6Hz)3H,1.40d(7Hz)3H,3.78 s2H,4.15q(6Hz)2H,4.75q(7Hz)1H, 5.20d(5Hz)1H,5.77dd(5;8Hz)1H, 6.8-7.5m3H,8.32s1H,9.08d(8Hz)1H. | — |
| 17 | — | −53.7° 0.255DMSO 22.5° C |
| 18 | — | −49.1° 0.520DMSO 23° C |
| 19 | — | — |
| 20 | 3.60br-s2H,3.87s2H,4.95d(5Hz) 1H,5.6-5.9m1H,7.23s5H,8.37s1H. | — |
| 21 | — | — |
| 22 | 3.78ABq(34;19Hz)2H,3.87s3H,4.54 s2H,5.02d(5Hz)1H,5.87ABq(9;5Hz) 1H,6.7-7.5m6H,8.40s1H.(CDCl$_3$) | — |

| No. | Acyl | =NOR' | m.p. | IR:$\nu_{max}^{Nujol}$(cm$^{-1}$) | UV:$\lambda_{max}^{EtOH}$nm($\epsilon$) |
|---|---|---|---|---|---|
| 23 | C$_6$H$_5$CHCO— \| NH$_2$ CF$_3$COOH | =NOCH$_3$ | ca. 270° C (dec.) | 1780,1708,1665, 1604,1540. | 300(18500) |
| 24 | C$_6$H$_5$CHCO— \| NHCOO \| tert-C$_4$H$_9$ | =NOCH(CH$_2$)$_5$ (cyclohexyl) (Hydrate) | 233–238° C | 3300,1786,1665. | 300.5(16700). |
| 25 | C$_6$H$_5$CHCO— \| NH$_2$ CF$_3$COOH | =NOCH(CH$_2$)$_5$ (cyclohexyl) | 159–165° C | 1780,1670. | — |
| 26 | C$_6$H$_5$CHCO— \| NHCOO \| tert-C$_4$H$_9$ | =NOCH$_2$COOH | 200–230° C (dec.) | 3305,1782,1678, 1604,1497. | 300(12000). |

TABLE II-continued
PHYSICAL CONSTANTS OF COMPOUNDS (I)

Structure: Acyl-NH on β-lactam fused to dihydrothiazine with CH=NOR' and COOH substituents

| No. | Acyl | =NOR' | m.p. | IR:$\nu_{max}^{Nujol}$(cm$^{-1}$) | UV:$\lambda_{max}^{EtOH}$nm($\epsilon$) |
|---|---|---|---|---|---|
| 27 | C$_6$H$_5$CHCO— with NH$_2$ · CF$_3$COOH | =NOCH$_2$COOH | 235–243° C (dec.) | 3200,1785,1677, 1610,1530. | 299.5(11500) |
| 28 | C$_6$H$_5$CHCO— with OH | =NOCH$_3$ | 125–130° C | 3320,1791,1754, 1707,1664,1600, 1563,1533,1518, 1454. | 301(18500). |
| 29 | N≡CCH$_2$CO— | =NOCH$_3$ (1/2 Hydrate) | 211–215° C (dec.) | 3265,2270,1798, 1714,1665,1602, 1551,1457. | 302(17800). |
| 30 | Cl$_3$CCH$_2$OCO— | =NOCH$_3$ | 187–190° C | 3322,3155,1801, 1720,1702,1609, 1574,1549. | 300(19200). |

| No. | NMR:$\delta^{d_6-DMSO}$ (Hz-Values show coupling consts.) | $[\alpha]_D^t$$^C$(c) |
|---|---|---|
| 23 | 3.67ABQ(28;18Hz)2H,3.85s3H,5.07 s1H,5.08d(5Hz)1H,5.83d(5Hz)1H, 7.48s5H,8.30s1H. (CD$_3$OD) | — |
| 24 | — | −72.6° 0.444CH$_3$OH 24.0° C |
| 25 | — | — |
| 26 | 1.40s9H,4.63s2H,5.10br1H,5.43brs 1H,5.90br1H,7.38brs5H,8.45brs 1H. | — |
| 27 | 4.58brs2H,5.05br1H,5.83br1H,7.47 s5H,8.30s1H,9.59d(8Hz)1H. | — |
| 28 | — | — |
| 29 | — | — |
| 30 | 3.83ABq(34;19Hz)2H,3.92s3H,4.78 s2H,5.09d(5Hz)1H,5.62d(5Hz)1H, 8.44s1H. (CDCl$_3$+CD$_3$DD) | — |

| No. | Acyl | =NOR' | m.p. | IR:$\nu_{max}^{Nujol}$(cm$^{-1}$) | UV:$\lambda_{max}^{EtOH}$nm($\epsilon$) |
|---|---|---|---|---|---|
| 31 | 2-(NO$_2$)-phenyl-S— | =NOCH$_3$ | 170–176° C (dec.) | 3367,3337,3302, 3087,1790,1760, 1725,1665,1591, 1565,1509. | 243(18900), 18(11900), 375(4730). |
| | (3-(α-oxyiminoethyl)-derivative) | | | | |
| 32 | thienyl-CH$_2$CO— | =NOCH$_3$ | 173–176° C | 3530,3260,1774, 1723,1655. | 237(12500), 288(9800), (CH$_3$OH) |
| | (7α-Methoxy derivatives) | | | | |
| 33 | thienyl-CH$_2$CO— | =NOCH$_3$ | 95–97° C (dec.) | 3460,3280,1777, 1679,1605,1521. | 236(10900), 303(13800). |
| 34 | thienyl-CH$_2$CO— | =NOCH$_2$COOH | 99–102° C (dec.) | 3260,1775,1727, 1679,1610,1527. | 236(11100), 301(12700). |
| 35 | thienyl-CH$_2$CO— | =NOCH$_2$COOCH$_3$ | 80–84° C (dec.) | 3480,3270,1780, 1735,1678,1605, 1520. | 236(12000), 301(14700). |
| 36 | thienyl-CH$_2$CO— | =NOCH$_2$CONH$_2$ | 110–117° C (dec.) | 3440,3280,1776, 1670,1603,1521. | 236(11100), 301.5(12400). |

| No. | NMR:$\delta^{d_6-DMSD}$ (Hz-Values show coupling consts.) | $[\alpha]_D^t$$^C$(c) |
|---|---|---|
| 31 | — | −7.3° 0.303DMSO 24.5° C |
| 32 | 2.02s3H,3.57brs2H,3.83s2H,3.87s 3H,5.04d(5Hz)1H,5.77d(5Hz)1H. (CDCl$_3$+CD$_3$OD) | +16.0° 0.207CH$_3$ 22.5° C |
| 33 | — | — |
| 34 | 3.38s3H,3.82s2H,4.62s2H,5.27s 1H,6.8–7.5m3H,8.23s1H,9.47s1H. | +67.2° 0.317CH$_3$ 24.0° C |
| 35 | 3.40s3H,3.68s3H,3.83s2H,4.73s 2H,5.28s1H,6.9–7.5m3H,8.25s1H, 9.47s1H. | +62.0° 0.313CH$_3$ 24.0° C |
| 36 | 3.42s3H,3.82s2H,4.47s2H,5.27s 1H,6.9–7.5m3H,8.30s1H,9.47s1H. | +65.1° 0.309CH$_3$ |

TABLE II-continued
PHYSICAL CONSTANTS OF COMPOUNDS (I)

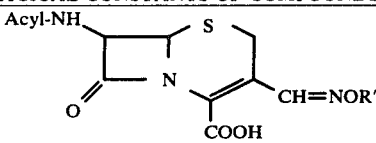

24.0° C

EXAMPLE III

Using a procedure similar to that in Example I or II, the following compounds are prepared.

3-carboxymethoxyiminomethyl-7β-acetamido-3-cephem-4-carboxylic acid,
3-methoxyiminomethyl-7β-(δ-carboxy-δ-tertiary butoxycarbonylamino-n-pentanoylamino)-3-cephem-4-carboxylic acid,
3-methoxyiminomethyl-7β-(δ-amino-δ-carboxy-n-pentanoylamino)-3-cephem-4-carboxylic acid,
3-methoxyiminomethyl-7β-(1-tetrazolylacetamido)-3-cephem-4-carboxylic acid,
3-hydroxyiminomethyl-7β-(α-amino-α-phenylacetamido)-3-cephem-4-carboxylic acid,
3-methoxyiminomethyl-7β-[α-(3-hydroxyphenyl)-glycylamino]-3-cephem-4-carboxylic acid,
3-carboxyiminomethyl-7β-[α-(4-hydroxyphenyl)acetamido]-3-cephem-4-carboxylic acid,
3-phenoxyiminomethyl-7β-[α-(3,5-dichloro-4-hydroxyphenyl)glycylamino]-3-cephem-4-carboxylic acid,
3-methoxyiminomethyl-7β-(N-methoxycarbonyl-α-phenylglycyclamino-3-cephem-4-carboxylic acid,
3-methoxyiminomethyl-7β-(N-sulfo-α-phenylglycylamino)-3-cephem-4-carboxylic acid,
3-methoxyiminomethyl-7β-(α-guanylureido)-phenylacetamido-3-cephem-4-carboxylic acid,
3-ethoxyiminomethyl-7β-(α-carboxyphenylacetamido)-3-cephem-4-carboxylic acid,
3-(2-chloropropoxyiminomethyl)-7β-(α-carboxy-3-hydroxyphenylacetamido)-3-cephem-4-carboxylic acid,
3-(4-chlorophenoxyiminomethyl)-7β-(2-sydnone-3-acetamido)-3-cephem-4-carboxylic acid,
3-methoxyiminomethyl-7β-phthalimido-3-cephem-4-carboxylic acid,
3-hydroxyiminomethyl-7β-phthalimido-3-cephem-4-carboxylic acid,
3-isobutoxyiminomethyl-7β-(2-nitrophenylsulfenylamino)-3-cephem-4-carboxylic acid,
3-methoxyiminomethyl-7β-isobornyloxycarbonylamino-3-cephem-4-carboxylic acid (m.p. 170°-190° C),
3-methoxyiminomethyl-7β-benzalimino-3-cephem-4-carboxylic acid,
3-methoxyiminomethyl-7β-(3-oxopyrrolidine-2-carbonamido)-3-cephem-4-carboxylic acid,
3-cyclohexyloxyiminomethyl-7β-(1-propyl-5-oxopyrrolidine-3-carbonamido)-3-cephem-4-carboxylic acid,
3-phenoxyiminomethyl-7β-(1-methyl-6-oxonicotinamido)-3-cephem-4-carboxylic acid,
3-(2-chloroethoxyiminomethyl)-7β-amino-3-cephem-4-carboxylic acid naphthalinesulfonate,
3-methoxymethoxyiminomethyl-7β-amino-3-cephem-4-carboxylic acid 3,4-dichlorobenzoate,
3-(N,N-dimethylaminomethoxyiminomethyl)-7β-amino-3-cephem-4-carboxylic acid hydrochloride,
3-(N,N-dimethylaminoethoxyiminomethyl)-7β-amino-3-cephem-4-carboxylic acid sulfate,
3-carboxymethoxyiminomethyl-7β-amino-3-cephem-4-carboxylic acid,
3-methoxyiminomethyl-7β-amino-3-cephem-4-carboxylic acid,
3-carbamoylmethoxyiminomethyl-7β-amino-3-cephem-4-carboxylic acid, and
3-carbethoxymethoxyiminomethyl-7β-amino-3-cephem-4-carboxylic acid.

EXAMPLE IV

To a solution of the O-methyl derivative of 3-formyl-7β-(2-thienylacetamido)-3-cephem-4-carboxylic acid hemiacetal lactone (148 mg) in tetrahydrofuran (10 ml) is added a solution of O-methylhydroxylamine hydrochloride (50 mg) in water (5 ml), and the mixture is kept at room temperature for 20 hours. The reaction mixture is evaporated to remove tetrahydrofuran, and the solid material which separates out is collected by filtration. Recrystallization of the solid from a mixture of ethyl acetate and ether gives 3-methoxyiminomethyl-7β-(2-thienylacetamido)-3-cephem-4-carboxylic acid (110 mg). m.p. 186°-189° C. Yield: 67%.

Using a procedure similar to that above, the same compound is prepared by reaction of the O-acetyl derivative of 3-formyl-7β-(2-thienylacetamido)-3-cephem-4-carboxylic acid hemiacetal lactone and O-methylhydroxylamine hydrochloride.

EXAMPLE V

To a solution of 3-dimethoxymethyl-7β-(2-thienylacetamido)-3-cephem-4-carboxylic acid (76 mg) in tetrahydrofuran (4 ml) is added a solution of O-methylhydroxylamine hydrochloride (23 mg) in water (1 ml), and the mixture is kept at room temperature for 10 hours. The reaction mixture is evaporated to remove tetrahydrofuran, and the separated solid material is collected by filtration. Recrystallization of the solid from a mixture of ethyl acetate and ether gives 3-methoxyiminomethyl-7β-(2-thienylacetamido)-3-cephem-4-carboxylic acid (61 mg). m.p. 186°-189° C. Yield: 80%.

EXAMPLE VI

To a solution of 3-methoxyiminomethyl-7β-(2-thienylacetamido)-3-cephem-4-carboxylic acid (10.1 g) in ethyl acetate (50 ml) is added a solution of potassium 2-ethylhexanoate (4.5 g) in propanol (8.9 ml), and the mixture is kept in a refrigerator for 15 hours. The crystals formed are collected by filtration, washed with ethyl acetate, and recrystallized from a mixture of methanol and ether to give potassium 3-methoxyiminomethyl-7β-(2-thienylacetamido)-3-cephem-4-carboxylate monohydrate (10.5 g). m.p. 206°-209° C. Yield: 91%.

EXAMPLE VII

A solution of 3-methoxyiminomethyl-7β-(2-thienylacetamido)-3-cephem-4-carboxylic acid (1 g) in water (100 ml) is neutralized with aqueous 2N-sodium hydroxide to pH 6.5. The solution is lyophylized to give a solid mass of sodium 3-methoxyiminomethyl-7β-(2-thienylacetamido)-3-cephem-4-carboxylate (1.1 g) which is readily soluble in water.

EXAMPLE VIII

A compound prepared in the foregoing Examples is dissolved in 0.0125 M aqueous sodium hydrogen carbonate solution to form the corresponding aqueous solution of the sodium salt, and the solution obtained is assayed for its antibacterial activity.

EXAMPLE IX i. To a solution of 3-ethoxyiminomethyl-7-(2-thienylacetamido)-3-cephem-4-carboxylic acid-1-oxide (100 mg) in N,N-dimethylformamide (5 ml) is added stannous chloride (100 mg) at 0° C under nitrogen atmosphere, and acetyl chloride (0.8 ml) is added dropwise to the stirred mixture. After 90 minutes, the reaction mixture is added a few piece of ice, and stirred for 10 minutes, and then extracted with ethyl acetate. The extract solution is washed with saturated saline solution and saturated aqueous sodium hydrogen carbonate, dried and evaporated to give residue which on recrystallization from a mixture of methylene chloride and ether gives 3-ethoxyiminomethyl-7-(2-thienylacetamido)-3-cephem-4-carboxylic acid. m.p. 177°–183° C (decomp.).

Using a procedure similar to that in Example IX (i) above, the Compounds 1–36 of Example II are prepared.

ii. To a solution of 7-amino-3-methoxyiminomethyl-3-cephem-4-carboxylic acid (134 mg) and triethylamine (0.1 ml) in chloroform (1 ml) is added 2-thienylacetyl chloride prepared from 2-thienylacetic acid (78 mg) and thionyl chloride (0.1 ml) in chloroform (1 ml), and the mixture is stirred at room temperature for 2 hours. The reaction mixture is diluted with water, adjusted to pH 2, and extracted with ethyl acetate. The extract solution is washed with water, dried and evaporated under reduced pressure. Treatment of the residue with ether gives 3-methoxyiminomethyl-7-(2-thienylacetamido)-3-cephem-4-carboxylic acid (161 mg; 82%). m.p. 186°–189° C.

Using a procedure similar to that in Example IX (ii) above, the Compounds 1–36 of Example II are prepared.

iii. To a solution of diphenylmethyl-3-methoxyiminomethyl-7-(2-thienylacetamido)-3-cephem-4-carboxylate (394 mg) in methylene chloride (11 ml) are added anisole (1.1 ml) and trifluoroacetic acid (1.1 ml) at 0° C under argon atmosphere, and the mixture is kept at the same temperature for 25 minutes, and at room temperature for 25 minutes. The reaction mixture is evaporated, and trituration of the residue in ether gives 3-methoxyiminomethyl-7-(2-thienylacetamido)-3-cephem-4-carboxylic acid (216 mg). m.p. 186°–189° C.

Using a procedure similar to that in Example IX (iii) above, the Compounds 1–36 of Example II are prepared from the corresponding diphenylmethyl esters.

iv. To a solution of diphenylmethyl 3-methoxyiminomethyl-7-(2-thienylacetamido)-3-cephem-4-carboxylate (887 mg) in benzene (48 ml) are added pyridine (0.26 ml) and phosphorous pentachloride (676 mg) in benzene (48 ml), and the mixture is stirred for 90 minutes. The mixture is diluted with methanol (96 ml), stirred for 2.5 hours, diluted with water (9.6 ml), stirred for 20 minutes, and evaporated at a temperature lower than 40° C. The residue is dissolved in ethyl acetate, washed with water, aqueous sodium hydrogen carbonate and water, dried and evaporated. The residue crystallizes from a mixture of ether and petroleum ether to give diphenylmethyl 3-methoxyiminomethyl-7-amino-3-cephem-4-carboxylate (639 mg; 94.2%). m.p. 135°–145° C.

Using a procedure similar to that in Example IX (iv) above, 3-oxyiminomethyl-7-optionally substituted alkanoylamino-3-cephem-4-carboxylic acid derivatives are converted to the corresponding 7-amino-3-oxyiminomethyl-3-cephem-4-carboxylic acid derivatives.

v. To a solution of diphenylmethyl 3-(diphenylmethoxycarbonylmethoxyiminomethyl)-7-(2-thienylacetamido)-3-cephem-4-carboxylate (187 mg) in methylene chloride (4 ml) are added anisole (0.8 ml) at 0° C, and trifluoroacetic acid (0.8 ml) under argon atmosphere, and the mixture is stirred for 10 minutes at room temperature. After evaporation of the methylene chloride and trifluoroacetic acid, the mixture is treated with ether to give 3-(carboxymethoxyiminomethyl)-7-(2-thienylacetamido)-3-cephem-4-carboxylic acid (86 mg). m.p. 158°–163° C (decomp.).

A solution of diphenylmethyl-3-methoxyiminomethyl-7-(N-tertiary butoxycarbonyl-α-phenylglycyl-)amino-3-cephem-4-carboxylate (64 mg) in ice-cooled trifluoroacetic acid (0.6 ml) and anisole (0.3 ml) is kept at room temperature for 25 minutes, and diluted with ether (5 ml) and petroleum ether (15 ml). The resulting crystals are collected by filtration and dried to give 3-methoxyiminomethyl-7-(α-phenylglycyl)amino-3-cephem-4-carboxylic acid trifluoroacetate (46 mg; 93.3%). m.p. about 270° C.

What we claim is:

1. A compound selected from the group consisting of (1) a compound of the formula:

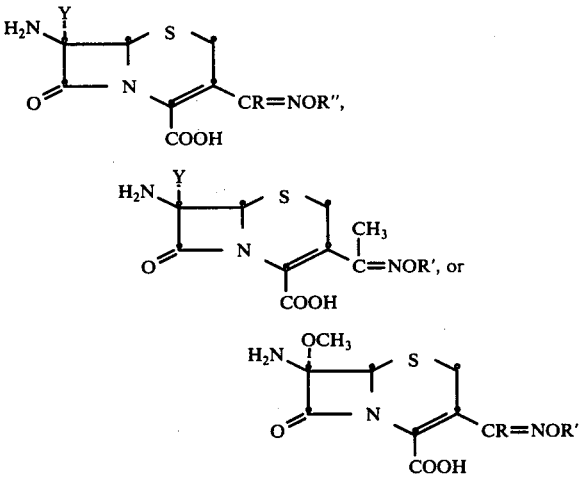

wherein
Y is hydrogen or methoxy
R is hydrogen or methyl;
R' is a member selected from the group consisting of hydrogen, methyl, ethyl, n-propyl, isopropyl, n- butyl, isobutyl, secondary butyl, tertiary butyl, n-pentyl, secondary pentyl, neopentyl, n-hexyl, 2-chloroethyl, 2-bromoethyl, 2-chloropropyl, 3-chloropropyl, 2,3-dichloropropyl, 4-bromobutyl, 2-chlorohexyl, methoxymethyl, methoxyethyl, methoxypropyl, ethoxyethyl, norbornyloxymethyl, propoxypropyl, methylthiomethyl, methylthioethyl, methylthiopropyl, N,N-dimethylaminoethyl, cyclobutyl, cyclopentyl, cyclohexyl, cycloheptyl, 4-methylcyclohexyl, benzyl, 4-nitrobenzyl, 4-methoxybenzyl, phenyl, tolyl, xylyl, mesityl, 4-ethylphenyl, α-naphthyl, β-naphthyl, vinyl, allyl, hexenyl, cyclohexenyl, ethinyl, propargyl, carboxymethyl, methoxycarbonylmethyl, ethoxycarbonylmethyl, propoxycarbonylmethyl, hexyloxycarbonylmethyl, butoxycarbonylmethyl, carbamoylmethyl, α-carboxyethyl, α-carbethoxyethyl, α-carbamoylethyl, and α-(N-methylcarbamoyl) ethyl; and R″ is a member selected from the group consisting of allyl, ethinyl, propargyl, benzyl, p-methoxybenzyl, carbamoylmethyl, and N-methylcarbamoyl, and (2) a derivative thereof bearing a protective grouping at the carboxyl group, said grouping being a member selected from the group consisting of a haloalkyl ester, a tertiary alkyl ester of 4–6 carbon atoms, a tertiary alkenyl ester of 5–7 carbon atoms, a tertiary alkynyl ester of 5–7 carbon atoms, benzyl ester, methoxybenzyl ester, nitrobenzyl ester, 3,5-di-(tertiary butyl)-4-hydroxybenzyl ester, acetoxymethyl ester, pivaloyloxy-methyl ester, benzhydryl ester, phenacyl ester, trimethylsilyl ester, succinimidomethyl ester, phthalimidomethyl ester, and the 1,2-di-isopropylhydrazide.

2. A compound claimed in claim 1, that is a compound selected from the group consisting of:

3-allyloxyiminomethyl-7β-amino-3-cephem-4-carboxylic acid, 3-ethinyloxyiminomethyl-7β-amino-3-cephem-4-carboxylic acid, 3-propargyloxyiminomethyl-7β-amino-3-cephem-4-carboxylic acid, 3-benzyloxyiminomethyl-7β-amino-3-cephem-4-carboxylic acid, 3-(p-methoxybenzyloxy)iminomethyl-7β-amino-3-cephem-4-carboxylic acid, 3-carbamoylmethoxyiminomethyl-7β-amino-3-cephem-4-carboxylic acid, 3-(N-methylcarbamoyl)methoxyiminomethyl-7β-amino-3-cephem-4-carboxylic acid, 3-(α-methoxyiminoethyl)-7β-amino-3-cephem-4-carboxylic acid, 3-(α-ethoxyiminoethyl)-7β-amino-3-cephem-4-carboxylic acid, 3-(α-carboxymethoxyiminoethyl)-7β-amino-3-cephem-4-carboxylic acid, 3-(α-carbamoylmethoxyiminoethyl)-7β-amino-3-cephem-4-carboxylic acid, 3-methoxyiminomethyl-7α-methoxy-7β-amino-3-cephem-4-carboxylic acid, 3-carboxymethoxyiminomethyl-7α-methoxy-7β-amino-3-cephem-4-carboxylic acid, 3-ethoxyiminomethyl-7α-methoxy-7β-amino-3-cephem-4-carboxylic acid, and 3-(α-methoxyiminoethyl)-7α-methoxy-7β-amino-3-cephem-4-carboxylic acid.

* * * * *